(12) United States Patent
Eltorai et al.

(10) Patent No.: US 10,918,487 B2
(45) Date of Patent: Feb. 16, 2021

(54) PROSTHETIC IMPLANT CAPS

(71) Applicant: Orthopedix, Inc., Louisville, KY (US)

(72) Inventors: Adam E. M. Eltorai, Louisville, KY (US); Ashok Seetharam, Louisville, KY (US); Vishal J. Thomas, Louisville, KY (US)

(73) Assignee: Orthopedix, Inc., Louisville, KY (US)

( * ) Notice: Subject to any disclaimer, the term of this patent is extended or adjusted under 35 U.S.C. 154(b) by 69 days.

(21) Appl. No.: 16/045,700

(22) Filed: Jul. 25, 2018

(65) Prior Publication Data

US 2020/0030101 A1    Jan. 30, 2020

(51) Int. Cl.
  *A61F 2/30*    (2006.01)
  *A61F 2/38*    (2006.01)
  *A61F 2/42*    (2006.01)
  *B33Y 80/00*   (2015.01)
  *A61F 2/50*    (2006.01)

(52) U.S. Cl.
  CPC ...... *A61F 2/30767* (2013.01); *A61F 2/30744* (2013.01); *A61F 2/30942* (2013.01); *A61F 2/38* (2013.01); *A61F 2/42* (2013.01); *A61F 2/5046* (2013.01); *A61F 2002/30621* (2013.01); *A61F 2002/30934* (2013.01); *B33Y 80/00* (2014.12)

(58) Field of Classification Search
  CPC ............ A61F 2/3872; A61F 2002/3895; A61F 2002/30985; A61F 2/30942; A61F 2002/3863; A61F 2/3859; A61F 2/38; A61F 2/30907; A61F 2002/30919
  See application file for complete search history.

(56) References Cited

U.S. PATENT DOCUMENTS

| | | | | |
|---|---|---|---|---|
| 4,151,615 A | * | 5/1979 | Hall | A61F 2/3877 623/20.19 |
| 5,171,282 A | * | 12/1992 | Pequignot | A61F 2/30907 623/20.35 |
| 5,768,134 A | * | 6/1998 | Swaelens | A61C 13/0004 700/121 |
| 6,214,051 B1 | * | 4/2001 | Badorf | A61F 2/3859 623/20.14 |
| 6,712,856 B1 | * | 3/2004 | Carignan | A61B 34/10 623/20.35 |
| 7,544,209 B2 | * | 6/2009 | Lotke | A61F 2/3877 623/20.18 |
| 7,833,274 B2 | * | 11/2010 | Popoola | A61F 2/38 623/20.14 |
| 7,837,739 B2 | | 11/2010 | Ogilvie | |
| D655,008 S | | 2/2012 | Gannoe et al. | |
| 8,843,229 B2 | | 9/2014 | Vanasse et al. | |

(Continued)

*Primary Examiner* — Alvin J Stewart
(74) *Attorney, Agent, or Firm* — Armis IP Law, LLC

(57) ABSTRACT

A prosthetic implant surface cap adapted for securement to an interface region of the prosthetic defined by articulating prosthetic implants. 3D printing or additive manufacturing is employed to form the surface cap adapted for securement to an identified interface region, in which the interface region is defined by engaging contact with adjacent skeletal structures in response to patient movement. The surface cap is disposed on the implant surface to contact the adjacent skeletal structures during articulated movement, and is adhered to the interface region of the prosthetic implant for absorbing and distributing the contact and frictional forces of the articulating skeletal members.

12 Claims, 4 Drawing Sheets

(56) References Cited

U.S. PATENT DOCUMENTS

| | | | |
|---|---|---|---|
| 9,119,613 B2 | 9/2015 | Gannoe et al. | |
| 9,381,085 B2* | 7/2016 | Axelson, Jr. | A61F 2/30771 |
| 9,622,868 B2* | 4/2017 | Lloyd | A61F 2/3859 |
| 9,655,727 B2* | 5/2017 | Wellings | A61F 2/3877 |
| 9,763,791 B2* | 9/2017 | Lawrynowicz | A61F 2/3609 |
| 10,085,839 B2* | 10/2018 | Wong | A61F 2/30942 |
| 2003/0114936 A1* | 6/2003 | Sherwood | A61F 2/30942 |
| | | | 623/23.58 |
| 2003/0216669 A1* | 11/2003 | Lang | A61F 2/30756 |
| | | | 600/587 |
| 2004/0204760 A1* | 10/2004 | Fitz | A61F 2/30756 |
| | | | 623/14.12 |
| 2005/0171604 A1* | 8/2005 | Michalow | A61F 2/38 |
| | | | 623/14.12 |
| 2006/0004460 A1* | 1/2006 | Engh | A61F 2/38 |
| | | | 623/20.21 |
| 2007/0100459 A1* | 5/2007 | Rhodes | A61F 2/3877 |
| | | | 623/20.19 |
| 2007/0100461 A1* | 5/2007 | Incavo | A61F 2/38 |
| | | | 623/20.19 |
| 2007/0100462 A1* | 5/2007 | Lang | A61F 2/38 |
| | | | 623/20.29 |
| 2007/0219641 A1* | 9/2007 | Dorr | A61F 2/30767 |
| | | | 623/22.42 |
| 2007/0233269 A1* | 10/2007 | Steines | A61B 5/107 |
| | | | 623/20.21 |
| 2007/0255288 A1* | 11/2007 | Mahfouz | A61B 5/1075 |
| | | | 606/102 |
| 2008/0058945 A1* | 3/2008 | Hajaj | A61F 2/38 |
| | | | 623/20.14 |
| 2008/0288081 A1* | 11/2008 | Scrafton | A61F 2/38 |
| | | | 623/20.33 |
| 2009/0088846 A1* | 4/2009 | Myung | A61F 2/4241 |
| | | | 623/14.12 |
| 2009/0222103 A1* | 9/2009 | Fitz | A61F 2/30942 |
| | | | 623/18.11 |
| 2009/0254190 A1 | 10/2009 | Gannoe et al. | |
| 2011/0022179 A1* | 1/2011 | Andriacchi | A61F 2/38 |
| | | | 623/20.18 |
| 2011/0035012 A1* | 2/2011 | Linares | A61F 2/30756 |
| | | | 623/18.11 |
| 2011/0066243 A1* | 3/2011 | Rivin | A61F 2/3872 |
| | | | 623/14.12 |
| 2011/0082548 A1* | 4/2011 | Assell | A61F 2/30756 |
| | | | 623/14.12 |
| 2011/0144760 A1* | 6/2011 | Wong | A61F 2/38 |
| | | | 623/20.14 |
| 2012/0209396 A1* | 8/2012 | Myung | C08G 77/38 |
| | | | 623/22.11 |
| 2012/0330429 A1* | 12/2012 | Axelson, Jr. | A61F 2/30771 |
| | | | 623/20.19 |
| 2014/0010951 A1* | 1/2014 | Vargas | C23C 16/045 |
| | | | 427/2.26 |
| 2014/0025181 A1 | 1/2014 | Vanasse et al. | |
| 2014/0135938 A1* | 5/2014 | Assell | A61F 2/3872 |
| | | | 623/20.31 |
| 2014/0316526 A1* | 10/2014 | Grotz | A61L 27/54 |
| | | | 623/20.17 |
| 2014/0371863 A1 | 12/2014 | Vanasse et al. | |
| 2015/0297350 A1* | 10/2015 | Robichaud | A61F 2/3859 |
| | | | 623/20.32 |
| 2016/0367369 A1* | 12/2016 | Alotaibi | A61F 2/30756 |
| 2017/0079721 A1* | 3/2017 | Zhao | A61F 2/36 |
| 2017/0143495 A1* | 5/2017 | Dunn | A61F 2/30771 |
| 2017/0202672 A1* | 7/2017 | Persaud | A61L 27/18 |
| 2017/0281355 A1* | 10/2017 | Winslow | A61F 2/30771 |
| 2017/0304056 A1* | 10/2017 | Gaignon | A61L 27/10 |
| 2018/0021138 A1* | 1/2018 | Estes | A61L 27/18 |
| | | | 623/16.11 |
| 2018/0028320 A1* | 2/2018 | Forsell | A61F 2/3607 |
| 2018/0064544 A1* | 3/2018 | Grotz | A61L 27/54 |
| 2018/0206995 A1* | 7/2018 | Kang | A61F 2/30756 |
| 2018/0271659 A1* | 9/2018 | Mansmann | A61F 2/30767 |
| 2018/0325683 A1* | 11/2018 | Logan | A61F 2/389 |
| 2019/0076254 A1* | 3/2019 | Essayed | A61F 2/2875 |
| 2019/0099273 A1* | 4/2019 | Servidio | A61F 2/30749 |
| 2019/0110905 A1* | 4/2019 | Cabot | A61B 17/157 |
| 2019/0240030 A1* | 8/2019 | Coulange | A61B 17/72 |
| 2019/0380838 A1* | 12/2019 | Ghodbane | A61F 2/30942 |
| 2020/0030101 A1* | 1/2020 | Eltorai | A61F 2/42 |

* cited by examiner

PROSTHETIC IMPLANT CAPS

BACKGROUND

Prosthetic appliances are surgical implants that replace natural skeletal structures in a patient. Natural skeletal structures such as bones, tendons and ligaments can be compromised by age, disease and traumatic injury, as well as other causes. Surgical replacement with an orthopedic implant attempts to duplicate the original bone or skeletal member so that the patient may continue to enjoy mobility and dexterity once provided by healthy skeletal members. Replacement orthopedic implants are particularly beneficial in articulated joints, as the natural skeletal structures include an engagement of skeletal structures that tend to experience a concentration of forces from human movements. Modern developments in CAD/CAM (computer aided design/computer aided manufacturing) has facilitated fabrication of these complex shapes.

SUMMARY

Configurations herein are based, in part, on the observation that orthopedic implants are employed to replace human skeletal members which often interface with other prosthetics or natural bone, as in a moving or pivoting juncture between bones. Unfortunately, conventional approaches to prosthetic skeletal members suffer from the shortcoming that exotic and/or expensive materials are often employed due to the requirement for biocompatibility and the need to withstand the stresses endured from intra-bone communication. Moving, or articulated members such as wrists, elbows, knees and ankles are articulated to provide a substantial range of motion while bearing considerable weight and related forces, depending on the musculature of the prosthetic patient. Accordingly, configurations herein substantially overcome the above-described shortcomings by providing a prosthetic implant cap adapted to engage a prosthetic implant at an interface region with an articulating structure, such as a bone joint. The implant cap absorbs and distributes the concentrated forces occurring due to the articulating skeletal members, allowing more freedom in material selection of the underlying prosthetic implant.

Configurations disclosed herein provide a method of forming a surface cap adapted for securement to an interface region of the prosthetic defined by articulating prosthetic implants. 3-dimensional (3D) printing or additive manufacturing is employed to form the surface cap adapted for securement to an identified interface region, in which the interface region is defined by engaging contact with adjacent skeletal structures in response to patient movement. The surface cap is disposed on the implant surface to contact the adjacent skeletal structures during articulated movement, and is adhered to the interface region of the prosthetic implant for absorbing and distributing the contact and frictional forces of the articulating skeletal members.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1A:
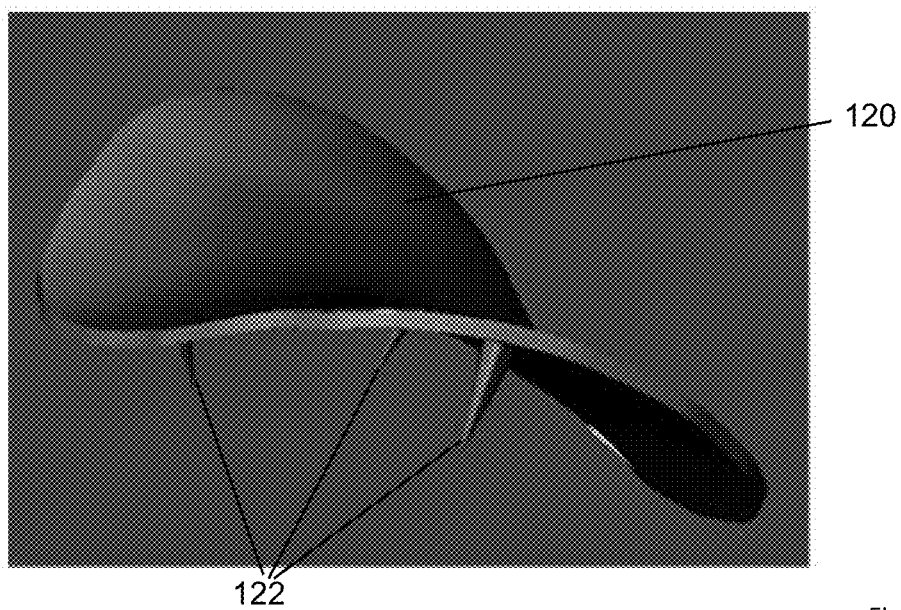
FIGS. 1a-1c are a diagram of a surface cap for a trapezium.
Figure 1B:
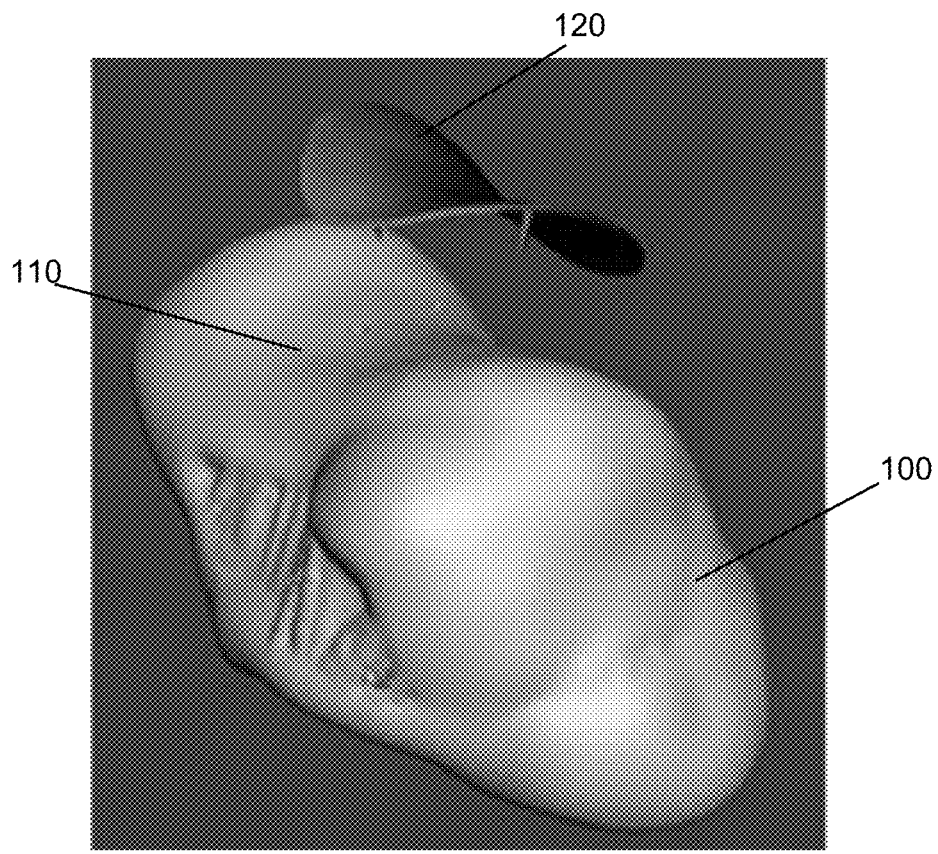
Figure 1C:
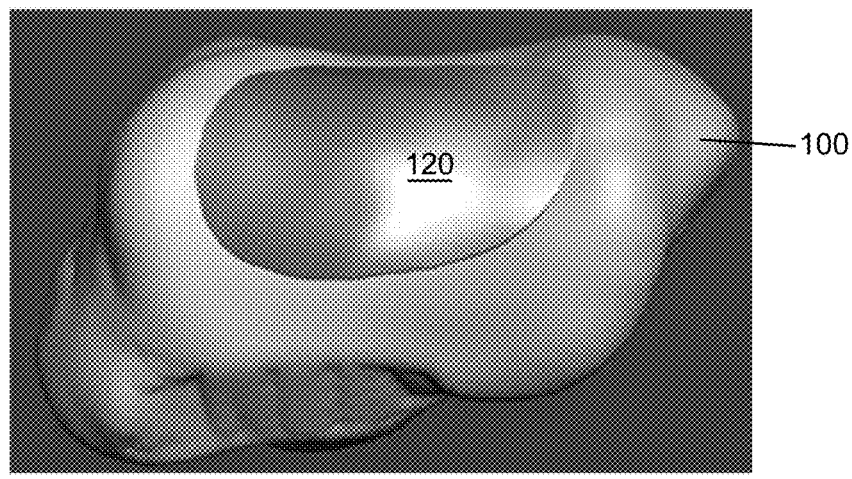

Depicted below is an example of a surgical implant cap fabrication and corresponding implantation procedure. FIGS. 1a-1c are a diagram of a surface cap for a trapezium. The disclosed approach may also be employed with prosthetic implants used in other suitable articulated arrangements. The method of forming a prosthetic implant cap includes selecting a biocompatible medium for a rendering a prosthetic implant 100, such that the prosthetic implant is rendered from 3-dimensional extrusion of the biocompatible medium based on scans of the anatomy of the patient receiving the implant. In contrast to conventional approaches using rare and/or expensive metals such as titanium, the disclosed prosthetic 100 is formed in an extruded manner on a 3-dimensional (3D) printing or rendering apparatus. Different surface characteristics of the 3D medium benefit from the implant cap at regions of substantial stress and friction. The friction and compressive forces at the interface region are accommodated by the surface cap so that they need not be absorbed directly by the implant material.

Accordingly, the 3D printer first renders the prosthetic implant using the biocompatible medium. On the prosthetic, an interface region 110 is identified, such that the interface region is defined by engaging contact with adjacent skeletal structures in response to patient movement. For example, the trapezium shares articulating (contact) regions with the adjacent wrist bones, including the scaphoid and thumb metacarpal. The formed surface cap is adapted for securement to the interface region, and is disposed to contact the adjacent skeletal structures during articulated movement. The surface cap may be adhered to the interface region 110 by securing with adhesives, screws and/or spikes 122.

Continuing to refer to FIGS. 1a-1c, forming the surface cap 120 includes selecting a biocompatible material different than the rendering medium of the prosthetic implant 100, and forming the surface cap 120 from the selected biocompatible material. Since the interface region experiences substantial stresses and forces which may not be present elsewhere in the prosthetic implant, the material selection for the surface cap 120 may have different requirements. For example, the prosthetic implant may be custom formed based on patient scans, and printed individually, rather than mass produced as are conventional implants. A readily extrudable medium which can be effectively rendered/printed using 3D and additive manufacturing techniques is thus a viable selection. As the interface region 110 encounters different, more directed forces, the use of an alternate medium for the surface cap 120 allows greater latitude in selection of the rendering medium for the implant 100 because the medium is not required to withstand the forces that the interface region 110 is subjected to. FIG. 1c shows the surface cap 120 secured to the prosthetic implant 100.

Figure 2:
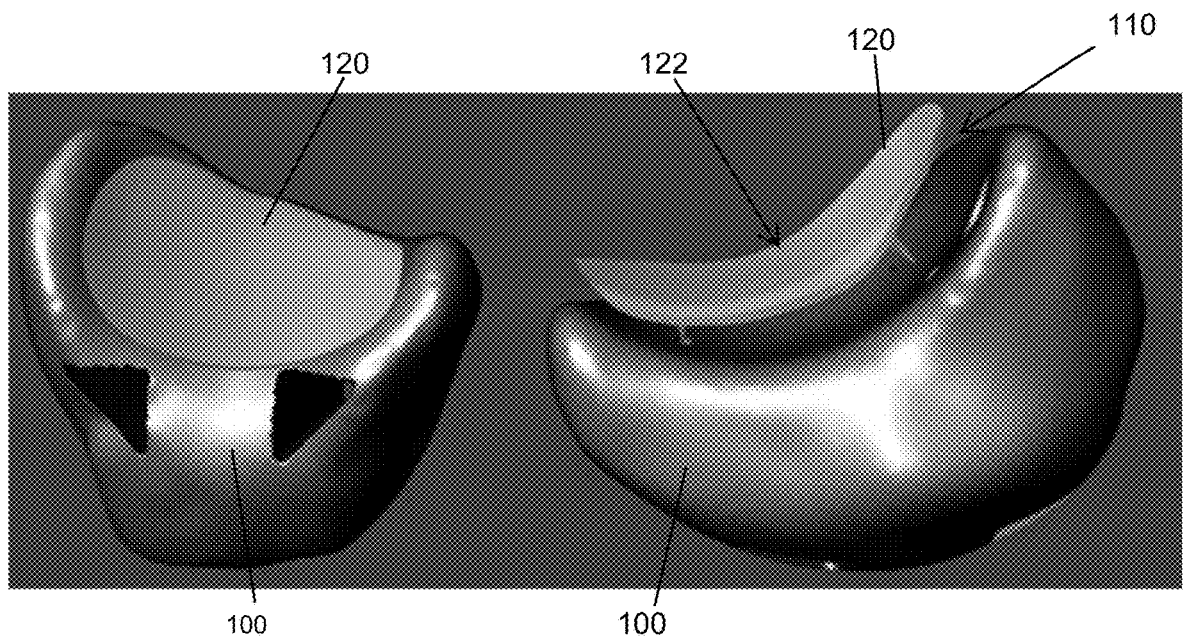
FIG. 2 is a diagram of a lunate surface cap.

In FIG. 2, a prosthetic implant 100 for a lunate exhibits a concave valley or depression defining an articulating region 110. Forming the surface cap 120 includes identifying a surface contour of the interface region 110, and forming the surface cap 120 based on the identified surface contour such as concave region 122. This may involve shaping the surface 120 cap to match the surface contour.

Figure 3:
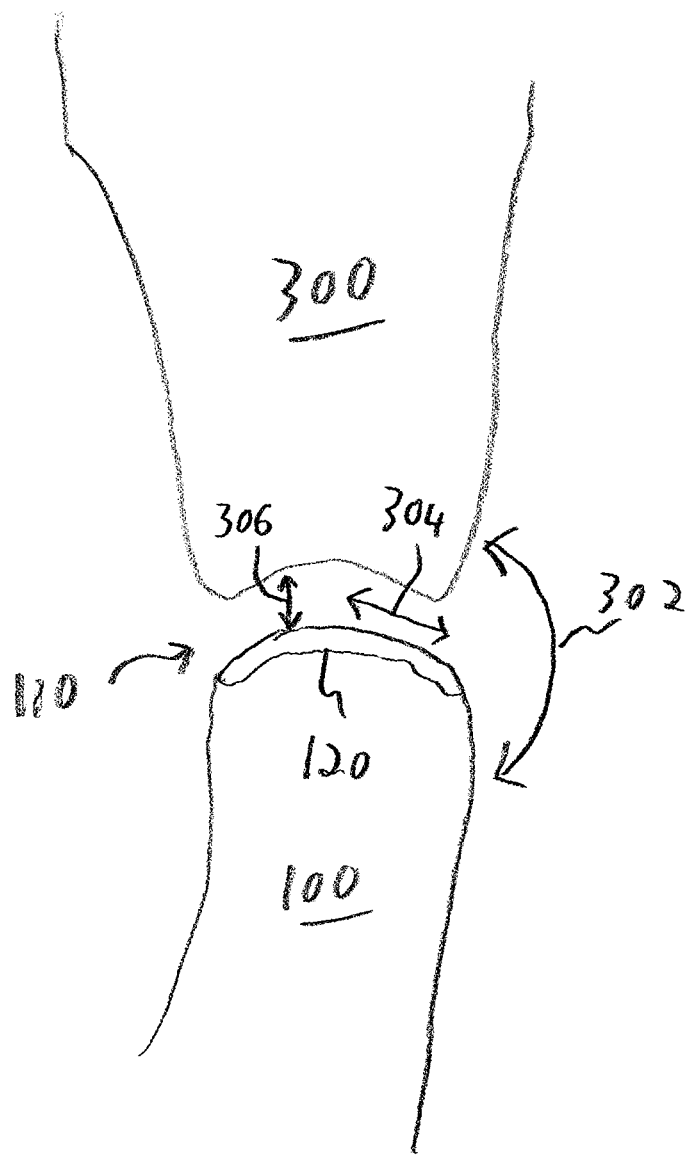
FIG. 3 shows a distribution of the forces in the interface region defining placement of the surface cap.

FIG. 3 shows a distribution of the forces in the interface region. An implant 100 and a natural skeletal member 300 (or another implant) proximately engage to define the interface region 110. As the bones articulate according to arrow 302, compressive forces 306 occur as one skeletal member 100, 300 disposes or forces the other. Further, the compressive force 306 drives the members together such that the members 100, 300 slideably engage and impose frictional forces 304.

In the example configuration, the surface cap 120 is formed from a material having a greater resilience to frictional engagement with the adjacent skeletal member than the rendering medium. It is also beneficial if the surface cap 120 has a greater resistance to compressive forces than the prosthetic implant. In this manner, the surface cap 120 enables use of materials that would otherwise not be acceptable for use in treating joint disease for attachment to native bone. In particular configurations, the surface cap 120 is formed from titanium or cobalt chrome (cobalt-chromium), selected due to their biocompatibility and strength.

Figure 4:
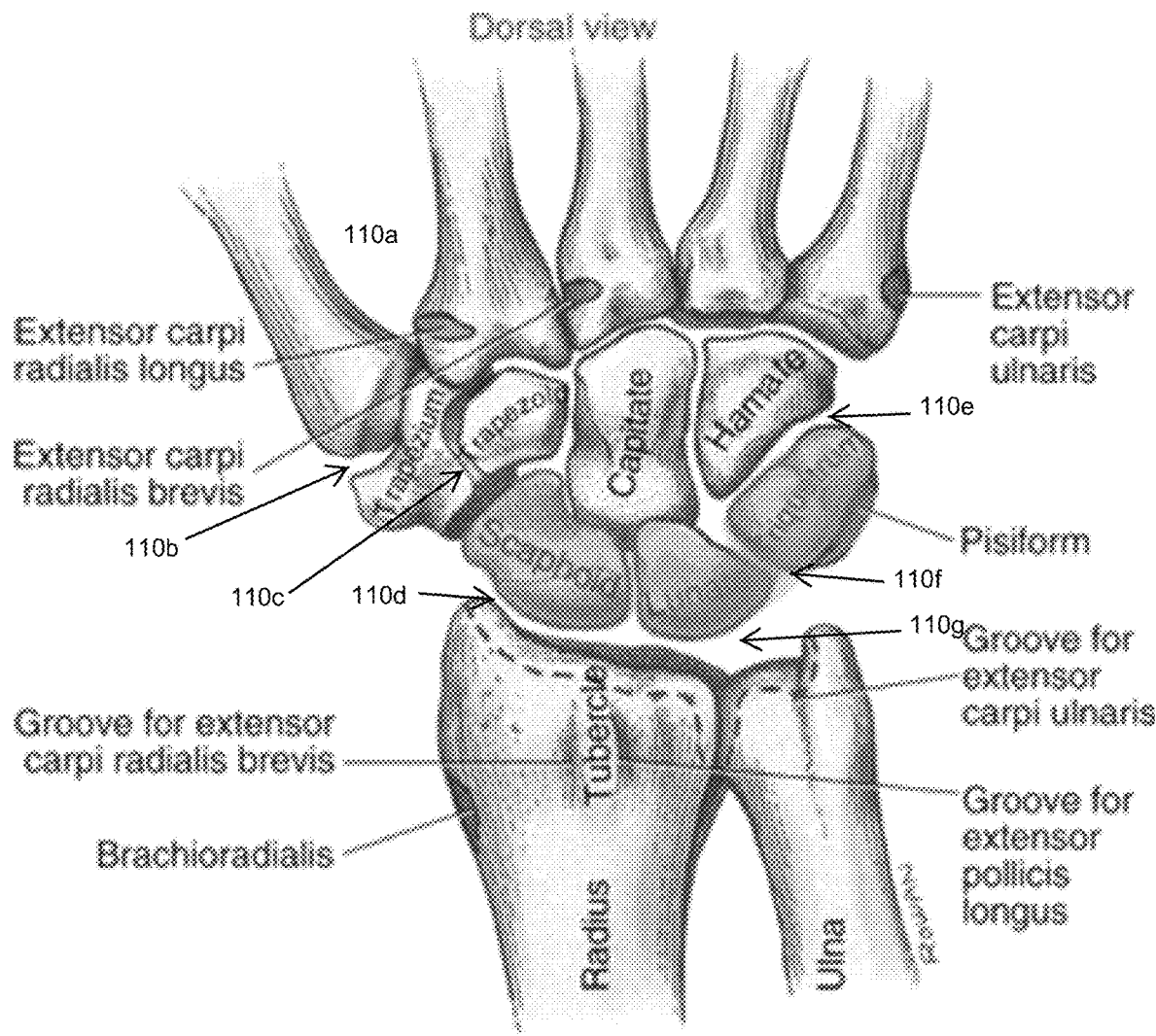
FIG. 4 shows interaction with adjacent skeletal members in the interface region.

FIG. 4 shows how the implant may interact with adjacent skeletal members in the interface region. Referring to FIGS. 1a-3, an implant 100 for the trapezium may have at least 4 interface regions 110-a . . . 110-d, including adjacencies to the first and second metacarpals 110a, 110b (thumb and index finger), trapezoid 110c, and scaphoid 110d. Similarly, an implant 110 for the lunate has interface regions 110e with the capitate, 110f with the triquetrum, and 110g with the arm bones radius and ulna. There may also be an interface region with the scaphoid, however certain procedures may treat the entire proximal carpal row (PCR) as a fused or unitary element.

The surface cap for a prosthetic implant may be formed by an apparatus in conjunction with the implant for attachment. The apparatus includes a raw material supply of a biocompatible medium for a rendering a prosthetic implant, such that the prosthetic implant is rendered from 3-dimensional extrusion of the biocompatible medium based on scans of the anatomy of the patient receiving the implant. The raw material supply is responsive to rendering the prosthetic implant using the biocompatible medium. An interface region on the prosthetic implant includes the articulation area or regions of surface stress, such that the interface region defined by engaging contact with adjacent skeletal structures in response to patient movement. An extrusion apparatus is configured to form the surface cap adapted for securement to the interface region, and is disposed to contact the adjacent skeletal structures during articulated movement. An attachment mechanism such as an elongated anchor, spike, or adhesive adheres the surface cap to the interface region. Alternatively, the surface cap could be formed from deformation of a planar material to form a contour matching the implant.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method of forming a prosthetic implant comprising:
   selecting a biocompatible medium for a rendering a prosthetic implant, the prosthetic implant rendered from 3-dimensional extrusion of the biocompatible medium based on scans of the anatomy of the patient receiving the implant;
   rendering the prosthetic implant using the biocompatible medium;
   identifying an interface region on the prosthetic implant, the interface region defined by engaging contact with adjacent skeletal structures in response to patient movement;
   forming a surface cap adapted for securement to the interface region, the surface cap disposed to contact the adjacent skeletal structures during articulated movement; and
   adhering the surface cap to the interface region.

2. The method of claim 1 further comprising securing the surface cap by at least one of adhesives, screws and spikes.

3. The method of claim 1 wherein forming the surface cap includes:
   selecting a biocompatible material different than the rendering medium of the prosthetic implant; and
   forming the surface cap from the selected biocompatible material.

4. The method of claim 1 wherein the surface cap is formed from a material having a greater resilience to frictional engagement with the adjacent skeletal member than the rendering medium.

5. The method of claim 4 wherein the surface cap has a greater resistance to compressive forces than the prosthetic implant.

6. The method of claim 1 further comprising:
   identifying a surface contour of the interface region; and
   forming the surface cap based on the identified surface contour.

7. The method of claim 6 further comprising shaping the surface cap to match the surface contour.

8. The method of claim 7 wherein the surface cap enables use of materials that would otherwise not be acceptable for use in treating joint disease for attachment to native bone.

9. The method of claim 7 wherein the surface cap is formed from titanium or cobalt-chromium.

10. A surface cap for a prosthetic implant comprising:
    a raw material supply of a biocompatible medium for a rendering a prosthetic implant, the prosthetic implant rendered from 3-dimensional extrusion of the biocompatible medium based on scans of the anatomy of the patient receiving the implant, the raw material supply responsive to rendering the prosthetic implant using the biocompatible medium;
    an interface region on the prosthetic implant, the interface region defined by engaging contact with adjacent skeletal structures in response to patient movement;
    an extrusion apparatus configured to form a surface cap adapted for securement to the interface region, the surface cap disposed to contact the adjacent skeletal structures during articulated movement; and
    an attachment mechanism to adhere the surface cap to the interface region.

11. The surface cap of claim 10 further comprising an elongated anchor extending from the surface cap and adapted for insertion in the implant.

12. The surface cap of claim 10 wherein the surface cap is formed from deformation of a planar material to form a contour matching the implant.

* * * * *